United States Patent
Erhard

(10) Patent No.: US 10,653,375 B2
(45) Date of Patent: May 19, 2020

(54) APPARATUS FOR DISPLAYING MEDICAL IMAGE DATA OF A BODY PART

(71) Applicant: KONINKLIJKE PHILIPS N.V., Eindhoven (NL)

(72) Inventor: Klaus Erhard, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 98 days.

(21) Appl. No.: 15/746,435

(22) PCT Filed: Sep. 1, 2016

(86) PCT No.: PCT/EP2016/070562
§ 371 (c)(1),
(2) Date: Jan. 22, 2018

(87) PCT Pub. No.: WO2017/037147
PCT Pub. Date: Mar. 9, 2017

(65) Prior Publication Data
US 2018/0199902 A1  Jul. 19, 2018

(30) Foreign Application Priority Data

Sep. 1, 2015  (EP) .................................... 15183299

(51) Int. Cl.
| | |
|---|---|
| *G06K 9/00* | (2006.01) |
| *A61B 6/00* | (2006.01) |
| *A61B 6/02* | (2006.01) |
| *A61B 8/00* | (2006.01) |
| *A61B 5/055* | (2006.01) |
| *G06K 9/46* | (2006.01) |

(Continued)

(52) U.S. Cl.
CPC .............. *A61B 6/463* (2013.01); *A61B 5/055* (2013.01); *A61B 6/025* (2013.01); *A61B 6/466* (2013.01);
(Continued)

(58) Field of Classification Search
None
See application file for complete search history.

(56) References Cited

U.S. PATENT DOCUMENTS

| 5,209,220 A | 5/1993 | Hiyama |
| 9,984,203 B2 | 5/2018 | Westin |
| (Continued) | | |

FOREIGN PATENT DOCUMENTS

| DE | 102011080768 | 2/2013 |
| EP | 1841223 | 10/2007 |
| (Continued) | | |

*Primary Examiner* — Fred H Hu
(74) *Attorney, Agent, or Firm* — Larry Liberchuk

(57) ABSTRACT

The present invention relates to an apparatus for displaying medical image data of a body part. It is described to provide (12) medical data of a body part, and subsets of medical image data from the medical data are determined (14). A plurality of measures of information content for the subsets of medical image data is determined (16), wherein a measure of information content is associated with a subset of medical image data. A plurality of weighting factors for the subsets of medical image data is determined (18), wherein a weighting factor is associated with a subset of medical image data and the weighting factor is determined as a function of the measure of information content for that subset of medical image data. Data representative of the subsets of medical image data is output (22) as a function of the plurality of weighting factors.

12 Claims, 5 Drawing Sheets

(51) Int. Cl.
  *G06K 9/52* (2006.01)
  *G16H 40/63* (2018.01)
  *G06T 5/50* (2006.01)
  *G16H 30/20* (2018.01)
  *G16H 30/40* (2018.01)
  *G06T 15/08* (2011.01)

(52) U.S. Cl.
  CPC ............ *A61B 6/502* (2013.01); *A61B 6/5235* (2013.01); *A61B 8/463* (2013.01); *G06K 9/4642* (2013.01); *G06K 9/4671* (2013.01); *G06K 9/52* (2013.01); *G06T 5/50* (2013.01); *G06T 15/08* (2013.01); *G16H 30/20* (2018.01); *G16H 30/40* (2018.01); *G16H 40/63* (2018.01); *A61B 6/486* (2013.01); *G06K 2209/051* (2013.01); *G06T 2207/10116* (2013.01); *G06T 2207/20221* (2013.01); *G06T 2207/30068* (2013.01)

(56) References Cited

U.S. PATENT DOCUMENTS

| | | |
|---|---|---|
| 2008/0015545 A1 | 1/2008 | Sanchez |
| 2008/0024599 A1 | 1/2008 | Hirakawa |
| 2008/0086028 A1* | 4/2008 | Matsui .................. A61B 1/0005 600/109 |
| 2008/0155451 A1 | 6/2008 | Lundstrom |
| 2009/0028409 A1* | 1/2009 | Tsukagoshi ............ A61B 6/032 382/131 |
| 2009/0190812 A1 | 7/2009 | Sano |
| 2010/0141654 A1 | 6/2010 | Neemuchwala |
| 2012/0136255 A1 | 5/2012 | Fan |
| 2013/0077840 A1* | 3/2013 | Blumfield ................ G06K 9/34 382/131 |
| 2014/0044421 A1* | 2/2014 | Sasaki .................. G11B 27/005 386/343 |
| 2014/0086471 A1 | 3/2014 | Ruth |

FOREIGN PATENT DOCUMENTS

| | | |
|---|---|---|
| EP | 2157790 | 2/2010 |
| JP | 2006149524 | 6/2006 |
| WO | 2009038948 | 3/2009 |
| WO | 2011044295 | 4/2011 |
| WO | 2013/009427 | 1/2013 |
| WO | 2013/078476 | 5/2013 |
| WO | 2013/123091 | 8/2013 |
| WO | 2014/092099 | 6/2014 |

* cited by examiner

APPARATUS FOR DISPLAYING MEDICAL IMAGE DATA OF A BODY PART

CROSS REFERENCE TO RELATED APPLICATIONS

This application is the U.S. National Phase application under 35 U.S.C. § 371 of International Application No. PCT/EP2016/070562, filed Sep. 1, 2016, published as WO 2017/037147 on Mar. 9, 2017, which claims the benefit of European Patent Application Number 15183299.5 filed Sep. 1, 2015. These applications are hereby incorporated by reference herein.

FIELD OF THE INVENTION

The present invention relates to an apparatus for displaying medical image data of a body part, to a medical system for displaying medical image data of a body part, and to a method for displaying medical image data of a body part, as well as to a computer program element and a computer readable medium.

BACKGROUND OF THE INVENTION

X-ray tomosynthesis is a technique that creates 3-D image representations. For example, when applied to mammography 3-D image representations of the breast can be created. A 3-D image representation is created from individual 2-D images, where the 2-D images are referred to as a stack. An individual 2-D image is referred to as a slice. Digital breast tomosynthesis both enables 3D imaging of the breast and offers the potential of increased cancer detection rates at reduced recall rates compared to standard 2D mammography screening. In a standard 2D mammography examination, a radiologist generally has to review four individual X-ray mammograms of the subject, i.e. two X-ray images for each breast. In digital breast tomosynthesis the number of X-ray images in the volume stack can be 20 or 30 times greater than the number of X-ray images required to be reviewed in 2-D mammography. Similar issues arise when viewing volumetric 3-D X-ray images other than tomosynthesis volume stacks, such as for example CT 3D volume stacks and magnetic resonance (MR) volume stacks.

The additional amount of data slows down the diagnostic reading of the acquired X-ray image data when transitioning from 2D to 3D screening, resulting in substantially larger reading times. Within a screening scenario it is therefore difficult to assess the larger amount of data in a comparable time without missing diagnostically relevant structures. Ways to overcome this issue have been proposed by showing an overview image in form of a 2D synthesized mammogram or presenting the reconstructed tomosynthesis slices in form of a cine-loop before the radiologist, radiographer, or clinician thoroughly reads the complete tomosynthesis volume in full resolution slice by slice. Similar issues relate to the viewing of other medical data, such as that acquired by CT systems, Magnetic Resonance systems and Ultrasound systems.

Furthermore, in relation to a single medical image, the clinician can also miss diagnostically relevant structures.

US2008/015545A1 discloses systems and methods for generating images of respective patients from multidimensional medical image data sets.

WO 2013/078476 A1 discloses a system and method for generating a 2D image using mammography and/or tomosynthesis image data.

SUMMARY OF THE INVENTION

It would be advantageous to have an improved technique for displaying medical image data of a body part.

The object of the present invention is solved with the subject matter of the independent claims, wherein further embodiments are incorporated in the dependent claims. It should be noted that the following described aspects of the invention apply also for the apparatus for displaying medical image data of a body part, the medical system for displaying medical image data of a body part, the method for displaying medical image data of a body part, and for the computer program element and the computer readable medium.

According to a first aspect, there is provided an apparatus for displaying medical image data of a body part, comprising:

an input unit;
a processing unit; and
an output unit.

The input unit is configured to provide the processing unit with medical data of a body part. The processing unit is configured to determine subsets of medical image data from the medical data. The processing unit is also configured to determine a plurality of measures of information content for the subsets of medical image data, wherein a measure of information content is associated with a subset of medical image data. The processing unit is also configured to determine a plurality of weighting factors for the subsets of medical image data, wherein a weighting factor is associated with a subset of medical image data and the weighting factor is determined as a function of the measure of information content for that subset of medical image data. The output unit is configured to output data representative of the subsets of medical image data as a function of the plurality of weighting factors. The information content is computed with the Shannon entropy. The processing unit is configured to determine a plurality of durations of time for the subsets of medical image data, wherein a duration of time is associated with a subset of medical image data and the duration of time is determined as a function of the weighting factor for that subset of medical image data; and wherein the output unit is configured to display the subsets of medical image data as a function of the plurality of durations of time In the discussion that follows, the medical data can be considered to be an X-ray image or a volume stack of X-ray images. In the first case, a subset of medical image data can be for example a zone, region or area of a single X-ray image such that another subset of medical image data can be another zone, region or area of the same X-ray image. Or, referring to the second example, a subset of medical image data can be an entire X-ray image or a portion of an entire X-ray image within a stack of X-ray images, such that another subset of medical image data is another X-ray image or a portion of another X-ray image in the stack of X-ray images. X-ray images are mentioned here, however, the medical data and subsets of medical image data equally applies to other medical data, such as one or more CT, MRI, or ultrasound images for example. The processing unit being configured to determine subsets of medical image data from the medical data can relate to: zones, regions or areas of a 2D image; to separate 2D images within a 3D stack of slices; to slabs, i.e. a combination of 2D images within a stack of slices, computed from the original data by re-arranging the data dependent on the information content ("combined images").

The information content of a subset of medical image data relates to the image information represented in at least a part of the subset of medical image data and additionally or alternatively relates to the brightness or intensity within at least a part of the subset of medical image data. Taking, for example an X-ray, in an example, the information content of the X-ray image relates to the image information represented in at least a part of the X-ray image and additionally or alternatively relates to the brightness or intensity within at least a part of the X-ray image. In an example, information content comprises features that have been extracted from the at least a part of an X-ray image, through the use of image processing. In other words, the information content in an X-ray image relates to the structure within that X-ray image upon which a clinician applies his skill and experience in interpreting whether the X-ray image contains information indicative of an anomaly.

The processing unit being configured to determine a plurality of measures of information content for the subsets of medical image data means that the processing unit determines a separate measure of information content for each subset of medical image data. In other words, in an example a separate measure of information content is determined for each X-ray image, or for a combination of X-ray images within a subset or for each zone, region or area of an X-ray image. To explain further, the information content within an image is calculated using Shannon Entropy, or an edge response filter for example. The measure of information content is then the result of that calculation for that image. A weighting factor can then be determined from that measure of information content. For example, the measure of information content could, in an example, be normalized to extend from 0 to 1 in order to determine the weighting factor. Or some other form of linear or non-linear transform could be applied to the measure of information content in determining the weighting factor. For example, the normalized information content as previously discussed could be squared in providing the weighting factor in order that those areas of high information content are provided with particularly high weights. In other words, the amount of time a clinician may want to spend looking at a particular image of part of an image may depend linearly on the information content within that image, or may depend non-linearly on the information content. The weighting factor takes this into account. The particular transform used, be it linear or non-linear relating the weighting factor to the measure of information content could be determined by a clinician and even be adjusted dependent upon feedback from experts in the field. It is however to be noted that the mechanism by which information content is determined in one image or image region, such as by Shannon entropy, is then applied to other images or image regions.

In an example, the apparatus can be used in tomosynthesis imaging or image display. In an example, the apparatus can be used in breast tomosynthesis imaging or image display. In an example, the apparatus can be used in digital tomosynthesis imaging or image display. In an example, the apparatus can be used in CT imaging or image display. In an example, the apparatus can be used in Magnetic Resonance (MR) imaging or image display. In an example, the apparatus can be used in Ultrasound imaging or image display. In other words, the apparatus can be applied to any kind of volumetric medical data, or to a single image frame.

In this manner, in an example the apparatus can be applied to X-ray Tomosynthesis, but the apparatus is not limited to such image data. For example, medical image data comprising an image or images could be produced by non-radiating modalities such as ultrasound or MRI and the like.

For example, by determining a weighting factor for sections of an image or for individual images, a proposed viewing time per image or section of image can be generated, and could be applied to lung cancer screening with CT, in which the radiologist time is a limited resource. The apparatus can also be used as a training tool for less experienced radiologists to help them optimize their workflow.

In this manner, the apparatus displays all of the subsets of medical image data (e.g. plurality of X-ray images), but does so as a function of, or in other words based on, a weighting factor for each of the subsets of medical image data (e.g. X-ray images) that is derived from a measure of information content for that subset of medical image data (e.g. X-ray image). In other words, the clinician is able to look at or review all of the subsets of medical image data (e.g. X-ray images or parts of an X-ray image) that have been taken, using their skill and knowledge to determine if a further examination is required, but by displaying the subsets of medical image data (e.g. plurality of X-ray images) as a function of the weighting factors the clinician can focus on those subsets of medical image data (e.g. X-ray images) that contain the most information. Therefore, the clinician can review the subsets of medical image data (e.g. X-ray images) more effectively in terms of being able to identify anomalies, and can also do this in a more timely manner. 3D imaging of the body part, such as a breast, is enabled with a potential reduction in the time needed by a clinician to review the data.

According to the invention, the processing unit is configured to determine a plurality of durations of time for the subsets of medical image data, wherein a duration of time is associated with a subset of medical image data and the duration of time is determined as a function of the weighting factor for that subset of medical image data. The output unit is configured to display the subsets of medical image data as a function of the plurality of durations of time.

In this manner, the durations of time for each subset of medical image data (e.g. X-ray image or part of an X-ray image) of the subsets of medical image data (e.g. plurality of X-ray images or X-ray image) can be determined. For example, the durations of time for each subset of medical image data (e.g. X-ray image) in subsets of medical image data (e.g. plurality of X-ray images) can be determined. In an example, the total display time is input by a user.

By this way, for example a cine loop of subsets of medical image data (e.g. X-ray images) can be displayed over a predetermined period of time, and where those subsets of medical image data (e.g. X-ray images) with more information content are shown for a longer period of time than those subsets of medical image data (e.g. X-ray images) with less information content. In other words, a time-between-frames can be determined for presenting the subsets of medical image data (e.g. X-ray images) as a cine-loop. In this manner, a clinician is more effectively able to determine if further analysis is warranted, and can do this in a timely manner. To put it another way, an optimal display time for each slice in a volume stack, or for each region of a slice, can be computed.

In other words, in an example a normalised entropy measure is mapped to a frame display time such that frames with high entropy are displayed longer that frames with low entropy.

In an example, the processing unit is configured to determine a plurality of indicators for the subsets of medical image data, wherein an indicator is associated with a subset of medical image data and the indicator is a function of the weighting factor for that subset of medical image data. The output unit is configured to output the plurality of indicators.

In an example, the medical data comprises a plurality of images, and wherein the processing unit is configured to determine at least one subset of medical image data that is a combined image of at least two of the plurality of images, and wherein the processing unit is configured to determine the at least one subset of medical image data that is a combined image such that the weighting factor for the at least one subset of medical image data that is a combined image is substantially the same as the weighting factor for a different subset of medical image data or substantially the same as a specified target value.

In an example, the processing unit is configured to: either, determine an information content for the subset of medical image data that is the combined image by determining information contents for the at least two of the plurality of images forming the combined image, and determine a weighting factor for the subset of medical image data that is the combined image by determining weighting factors for the at least two of the plurality of images forming the combined image and summing those weighting factors; or, determine an information content for the subset of medical image data that is the combined image by determining a single information content for the combined image, and determine a weighting factor for the subset of medical image data that is the combined image by determining a single weighting factor for the combined image.

In this manner, a reduced number of subsets of medical image data (e.g. X-ray images) of variable slab thickness can be determined, each having substantially the same information content and as such the clinician can spend, or expect to spend, the same time reviewing each.

According to a second aspect, there is provided a medical system for displaying medical image data of a body part, the system comprising:
    an image acquisition unit;
    an apparatus for displaying medical image data of a body part according to the first described aspect and any of the preceding examples; and
    a display unit. The image acquisition unit is configured to provide the medical image data of a body part. The display unit is configured to display the subsets of medical image data.

According to a third aspect, there is provided a method for displaying medical image data of a body part, comprising:
a) providing medical data of a body part;
b) determining subsets of medical image data from the medical data;
c) determining a plurality of measures of information content for the subsets of medical image data, wherein a measure of information content is associated with a subset of medical image data;
d) determining a plurality of weighting factors for the subsets of medical image data, wherein a weighting factor is associated with a subset of medical image data and the weighting factor is determined as a function of the measure of information content for that subset of medical image data and wherein the information content is computed with the Shannon entropy;
e) determining a plurality of durations of time for the subsets of medical image data, wherein a duration of time is associated with a subset of medical image data and the duration of time is determined as a function of the weighting factor for that subset of medical image data; and wherein the output unit is configured to display the subsets of medical image data as a function of the plurality of durations of time; and
f) outputting of data representative of the subsets of medical image data as a function of the plurality of weighting factors.

In an example, the method comprises the step of:
g) determining a plurality of indicators for the subsets of medical image data, wherein an indicator is associated with a subset of medical image data and the indicator is a function of the weighting factor for that subset of medical image data; and wherein the output unit is configured to output the plurality of indicators.

In this manner, indicators are provided that are linked to the information content in subsets of medical image data (e.g. X-ray images or parts of an X-ray image) and can be used to differentiate between different subsets of medical image data (e.g. X-ray images or parts of an X-ray image) or used to determine when to view a new subset of medical image data (e.g. X-ray image or part of an X-ray image) on the basis of a measure of the information content in those subsets of medical image data (e.g. X-ray images or parts of an X-ray image). In other words, an indicator is output linked to or indicating the information content of a current subset of medical image data (e.g. X-ray image or part of an X-ray image) with respect to other subsets of medical image data (e.g. X-ray images or parts of an X-ray image) in a sequence or medical data or medical image.

In an example step f) comprises displaying the subsets of medical image data, and displaying and/or sounding an indicator of the plurality of indicators that is associated with a subset of medical image data along with the display of the subset of medical image data.

In other words, an indicator is displayed linked to or indicating the information content of a current subset of medical image data (e.g. part of or a complete or combined X-ray image) with respect to other subsets of medical image data (e.g other parts of an X-ray image, or other X-ray images in a sequence). In this manner, the clinician is provided with simple to interpret visual and/or audio information relating to how seriously they should examine a particular subset of medical image data (e.g. X-ray image), and whether they should consider reviewing the next subset of medical image data, for example review the next image in a sequence or the newt part of an image.

In an example, the medical data comprises a plurality of images, and wherein step b) comprises determining at least one subset of medical image data that is a combined image of at least two of the plurality of images, and wherein the method comprises:
h) determining the at least one subset of medical image data that is a combined image such that the weighting factor for the at least one subset of medical image data that is a combined image is substantially the same as the weighting factor for a different subset of medical image data or substantially the same as a specified target value.

In an example, step c) comprises determining an information content for the subset of medical image data that is the combined image by determining information contents for the at least two of the plurality of images forming the combined image, and wherein step d) comprises determining a weighting factor for the subset of medical image data that is the combined image by determining weighting factors for the at least two of the plurality of images forming the combined image and summing those weighting factors.

In an example, step c) comprises determining an information content for the subset of medical image data that is the combined image by determining a single information content for the combined image, and wherein step d) comprises determining a weighting factor for the subset of medical image data that is the combined image by determining a single weighting factor for the combined image.

In this manner, those subsets of medical image data (e.g. X-ray images) with little image content can be combined together into one or a number of a combined images (e.g. combined X-ray image(s)) with an increased information content, thereby reducing the total number of images and therefore speeding up the review process, and also the clinician will better be able to determine from the combined image whether there is for example an abnormality because the image or information content for that combined image has been increased. In other words, in an example the plurality of images is transformed into a plurality of combined images, where the number of combined images is less than the number of images and each combined image contains roughly the same amount of information. In this manner, the clinician is provided with fewer frames to inspect and can expect to spend approximately the same amount of time reviewing each frame, because the combined images (slabs of variable thickness) each have substantially the same measure of information content. In an example, the plurality of combined images is displayed.

In other words, images or slices (e.g. X-ray images) are combined in slabs of variable slice thickness, which is computed such that each slab contains the same amount of image information or information content and has the same weighting factor. Put another way, in an example several neighbouring slices in a stack are combined to form a slab, such that the entropy of each slab is approximately equal. The clinician can then view a reduced number of images (e.g. X-ray images) in assessing the full image set, thereby taking less time. In this manner, each image can be shown or viewed for the same length as time as other images, because each contains approximately the same amount of information. According to another aspect, there is provided a computer program element controlling apparatus as previously described which, in the computer program element is executed by processing unit, is adapted to perform the method steps as previously described. According to another aspect, there is provided a computer readable medium having stored computer element as previously described. Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
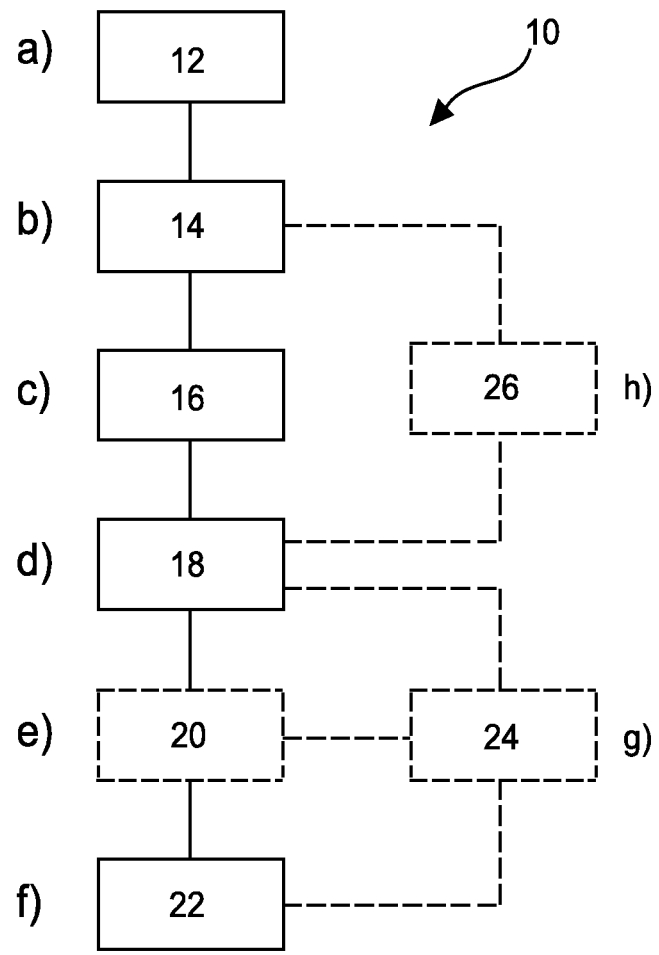
FIG. 1 shows an example of a method for displaying medical image data of a body part.

FIG. 1 shows a method 10 for displaying medical image data of a body part in its basic steps. The method comprises the following:

In a providing step 12, also referred to as step a), medical data of a body part is provided.

In a first determining step 14, also referred to as step b), subsets of medical image data from the medical data are determined.

In a second determining step 16, also referred to as step c), a plurality of measures of information content for the subsets of medical image data is determined, wherein a measure of information content is associated with a subset of medical image data.

In a third determining step 18, also referred to as step d), a plurality of weighting factors for the subsets of medical image data is determined, wherein a weighting factor is associated with a subset of medical image data and the weighting factor is determined as a function of the measure of information content for that subset of medical image data.

In an outputting step 22, also referred to as step f), data representative of the subsets of medical image data is output as a function of the plurality of weighting factors.

In an example, the method comprises the step of determining a plurality of time factors for the subsets of medical image data (e.g. plurality of X-ray images), wherein a time factor is associated with a subset of medical image data (e.g. X-ray image) and the time factor is determined as a function of the weighting factor for that subset of medical image data (e.g. X-ray image).

According to an example, the method comprises the following:

In a determining step 20, also referred to as step e), a plurality of durations of time for the subsets of medical image data is determined, wherein a duration of time is associated with a subset of medical image data and the duration of time is determined as a function of the weighting factor for that subset of medical image data. The output unit is configured to display the subsets of medical image data as a function of the plurality of durations of time.

According to an example, the method comprises the following:

In a determining step 24, also referred to as step g), a plurality of indicators for the subsets of medical image data is determined, wherein an indicator is associated with a subset of medical image data and the indicator is a function of the weighting factor for that subset of medical image data. The output unit is configured to output the plurality of indicators.

In an example, a subset of medical image data (e.g. X-ray image) of the subsets of medical image data (e.g. plurality of X-ray images) is output along with an indicator for that subset of medical image data (e.g. X-ray image). In an example, each of the subsets of medical image data (e.g. X-ray image) of the subsets of medical image data (e.g.

plurality of X-ray image) is output along with an indicator for each of the subsets of medical image data (e.g. plurality of X-ray images). For example, a subset of medical image data (e.g. X-ray image) of the subsets of medical image data (e.g. plurality of X-ray images) is output along with an indicator for that subset of medical image data (e.g. X-ray image). For example, each of the subsets of medical image data (e.g. X-ray images) of the subsets of medical image data (e.g. plurality of X-ray images) is output along with an indicator for each of the subset of medical image data (e.g. X-ray images).

In an example, the plurality of indicators comprises at least one visual marker. In an example, the plurality of indicators comprises at least one audio marker. In an example, the indicator is a function of the time factor for that subset of medical image data (e.g. X-ray image); and wherein the output unit is configured to output the plurality of indicators. In an example, the indicator is a function of the duration of time for that subset of medical image data (e.g. X-ray image); and wherein the output unit is configured to output the plurality of indicators. For example, the indicator is a function of the time factor for that subset of medical image data (e.g. X-ray image); and wherein the output unit is configured to output the plurality of indicators. For example, the indicator is a function of the duration of time for that subset of medical image data (e.g. X-ray image); and wherein the output unit is configured to output the plurality of indicators.

According to an example, step f) comprises displaying the subsets of medical image data, and displaying and/or sounding an indicator of the plurality of indicators that is associated with a subset of medical image data along with the display of the subset of medical image data.

In an example, step f) comprises displaying the subsets of medical image data (e.g. X-ray image), and displaying an indicator of the plurality of indicators that is associated with a subset of medical image data (e.g. X-ray image) along with the display of the subset of medical image data (e.g. X-ray image). For example, step f) comprises displaying the plurality of X-ray images, and displaying an indicator of the plurality of indicators that is associated with an X-ray image of the plurality of X-ray images along with the display of the X-ray image.

In an example, the indicator for a subset of medical image data (e.g. X-ray image) is proportional to the weighting factor for that subset of medical image data (e.g. X-ray image). In an example, the indicator for a subset of medical image data (e.g. X-ray image) is equal to the weighting factor for that subset of medical image data (e.g. X-ray image). In an example, the indicator for a subset of medical image data (e.g. X-ray image) is a function of the time factor for that subset of medical image data (e.g. X-ray image). In an example, the indicator for a subset of medical image data (e.g. X-ray image) is proportional to the time factor for that subset of medical image data (e.g. X-ray image). In an example, the indicator for a subset of medical image data (e.g. X-ray image) is equal to the time factor for that subset of medical image data (e.g. X-ray image). In an example, the indicator for a subset of medical image data (e.g. X-ray image) is a function of the duration of time determined for that subset of medical image data (e.g. X-ray image). In an example, the indicator for a subset of medical image data (e.g. X-ray image) is proportional to the duration of time for that subset of medical image data (e.g. X-ray image). In an example, the indicator for a subset of medical image data (e.g. X-ray image) is equal to the duration of time for that subset of medical image data (e.g. X-ray image). As discussed above, in all of these examples the subsets of medical image data can be parts of a single image or be a number of separate images, where those separate images can comprise combined images and where those images can be X-ray, ultrasound, MRI and be acquired for example by a tomography arrangement, a CT arrangement, an MRI arrangement or an ultrasound arrangement.

In an example, the plurality of indicators comprises a plurality of colours. In an example, a colour is associated with a range of weighting factors. For example, green is associated with weighting factors from 0 to 0.3, and yellow is associated with weighting factors from 0.4 to 0.7, and red is associated with weighting factors from 0.8 to 1.0. In other words, high weights correspond to high information content, determined for example on the basis of Shannon entropy, and a traffic light like system of colours from green to red can be used to help the clinician determine how they should look at each image or image part. In an example, a coloured dot or region is applied to a region of a subset of medical image data (e.g. X-ray image) being displayed, or separately displayed on a different display, which if red would indicate that the clinician may want to look at the image in detail, and if green the clinician may want to review the subset of medical image data (e.g. X-ray image) rapidly or not at all. A plurality of colours could also be associated with the time factors or the durations of time.

In an example, the plurality of indicators comprises at least one colour. In an example, when a subset of medical image data (e.g. X-ray image) is being displayed a yellow coloured dot is applied to a region of the subset of medical image data (e.g. X-ray image), or separately displayed on a different display, for a duration of time starting from when the subset of medical image data (e.g. X-ray image) was first displayed that is equal to the duration of time determined for that subset of medical image data (e.g. X-ray image). In an example when a time has passed that is equal to the duration of time determined for that subset of medical image data (e.g. X-ray image), the coloured region changes its colour from yellow to green.

In this manner the clinician is provided with simple to interpret colour coded information relating to how seriously they should examine a particular subset of medical image data (e.g. X-ray image), and whether they should consider reviewing the next subset of medical image data, for example the next image in a sequence or the next part of an image. In an example, the plurality of indicators comprises a plurality of numbers. For example, the weighting factor for a subset of medical image data (e.g. X-ray image) can be displayed on that subset of medical image data (e.g. X-ray image), or the time factor for that subset of medical image data (e.g. X-ray image) can be displayed on that subset of medical image data (e.g. X-ray image), or the duration of time for that subset of medical image data (e.g. X-ray image) can be displayed on that subset of medical image data (e.g. X-ray image). In other examples, the plurality of indicators comprises graphical representations of bars, clocks, dots of different sizes as would be appreciated by the skilled person.

In an example, step f) comprises displaying the subsets of medical image data (e.g. X-ray image), and sounding an indicator of the plurality of indicators that is associated with a subset of medical image data (e.g. X-ray image) along with the display of the subset of medical image data (e.g. X-ray image). For example, step f) comprises displaying the plurality of X-ray images, and sounding an indicator of the plurality of indicators that is associated with an X-ray image of the plurality of X-ray images along with the display of the X-ray image. In an example, the sounding of the indicator comprises a loudspeaker making a beeping noise, or other similar noise intended to attract a user's attention. In an example, the indicator comprises an audio signal.

In an example, the indicator for a subset of medical image data (e.g. X-ray image) is a function of the time factor for that subset of medical image data (e.g. X-ray image). In an example, the indicator for a subset of medical image data (e.g. X-ray image) is a function of the duration of time determined for that subset of medical image data (e.g. X-ray image). In an example, the indication of sound has a volume that is linked to the measure of information content, such that a subset of medical image data (e.g. X-ray image) that warrants detailed investigation can have a loud beep sounding as it is shown, whilst a subset of medical image data (e.g. X-ray image) with little image content can have an associated beep of minimal volume. In an example, the volume of sound for a subset of medical image data (e.g. X-ray image) is linked to the weighting factor for that subset of medical image data (e.g. X-ray image), for example is proportional to the weighting factor. In an example, the tone or frequency of the audio signal is linked to the weighting factor.

In an example, a clinician viewing a subset of medical image data (e.g. X-ray image) is provided with an audio signal that sounds after a duration of time from when the subset of medical image data (e.g. X-ray image) was first displayed that is equal to the duration of time determined for that subset of medical image data (e.g. X-ray image). In this manner, the clinician is given an indication that they may wish to view the next subset of medical image data, for example the next image in a sequence or the next part of an image, and is provided with information that a subset of medical image data does not warrant detailed investigation or indeed does warrant a detailed review.

In other words, an indicator can be heard that is linked to or indicating the information content of a current subset of medical image data (e.g. X-ray image) with respect to other subsets of medical image data (e.g. X-ray images in a sequence). In this manner, the clinician is provided with audio information relating to when they may wish to view a next image in a sequence or next part of an image. Or for images with little information content, they will be provided with information soon after reviewing the image or part of an image helping them decide to move on to the next image or next part of that image. However, for an image with a lot of image content or part of image, and which they may wish to review in detail, audio information is provided in delayed form reinforcing to the clinician that they should indeed review this particular slide or part of slide in great detail.

In an example, there is provided a method for displaying images of a body part, comprising: providing a plurality of images of a body part relating to a plurality of depths within the body part, wherein an image is associated with a depth within the body part; determining a plurality of measures of information content for the plurality of images, wherein a measure of information content is associated with an image; determining a plurality of weighting factors for the plurality of images, wherein a weighting factor is associated with an image and the weighting factor is determined as a function of the measure of information content for that image; and outputting of data representative of the plurality of images as a function of the plurality of weighting factors.

In an example, there is provided a method for displaying images of a body part, comprising: providing a plurality of images of a body part relating to a plurality of depths within the body part, wherein an image is associated with a depth within the body part; determining a first combined image from a first subset of images of the plurality of images, and determining at least one second combined image from at least a second subset of images of the plurality of images containing images different to those in the first subset of images; determining a measure of information content for the first combined image, and determining at least one measure of information content for the at least one second combined image; determining the first combined image and determining the at least one second combined image such that the measure of information content for the first combined image is substantially the same as the at least one measure of information content for the at least one second combined image; and outputting of data representative of the first combined image and the at least one second combined image.

In an example, there is provided a method for displaying an image of a body part, comprising: providing an image of a body part, wherein the image is associated with a depth within the body part; dividing the image into a plurality of regions; determining a plurality of measures of information content for the plurality of regions, wherein a measure of information content is associated with a region; and displaying the image along with an indicator, wherein the indicator is displayed as a function of the plurality of measures of information content.

According to an example, the medical data comprises a plurality of images, and wherein step b) comprises determining at least one subset of medical image data that is a combined image of at least two of the plurality of images, and wherein the method comprises:

In a determining step 26, also referred to as step h), the at least one subset of medical image data that is a combined image is determined such that the weighting factor for the at least one subset of medical image data that is a combined image is substantially the same as the weighting factor for a different subset of medical image data or substantially the same as a specified target value.

In an example, subsets of medical image data (e.g. some of which are combined X-ray images) are determined such that the weighting factors for all of the subsets of medical image data are substantially the same. In an example, an iterative process is applied in order that the subsets of medical image data are determined such that the weighting factors for all of the subsets of medical image data are substantially the same. In an example, a substantial proportion of the subsets of medical image data are combined images of at least two of the plurality of images. In an example, all of the subsets of medical image data are combined images.

According to an example, step c) comprises determining an information content for the subset of medical image data that is the combined image by determining information contents for the at least two of the plurality of images forming the combined image. In this example, step d) comprises determining a weighting factor for the subset of medical image data that is the combined image by determining weighting factors for the at least two of the plurality of images forming the combined image and summing those weighting factors.

According to an example, step c) comprises determining an information content for the subset of medical image data that is the combined image by determining a single information content for the combined image. In this example, step d) comprises determining a weighting factor for the subset of medical image data that is the combined image by determining a single weighting factor for the combined image.

In an example, neighbouring slices or images in a stack are combined. For example, slices are only combined if they relate to an adjacent depth of the body part. In an example, the means by which the measure of information content is determined is linear, in that individual images (e.g. X-ray image) can be combined together and the sum of the measures of information content for the individual images (e.g. X-ray images) is substantially equal to the measure of information content for the combined image (e.g. combined X-ray image). In an example, the sum of the weighting factors for the individual images (e.g. X-ray images) that have been combined is substantially equal to the weighting factor for the combined image (e.g. combined X-ray image). In an example, the at least one subset of medical image data that is a combined image (e.g. combined X-ray image or images) and the other subsets of medical image data (e.g. the plurality of images that have not been formed into combined images) are displayed.

In an example, the combination of neighbouring slices or images (e.g. X-ray images) can be determined using a weighting algorithm, which takes the local entropy into account.

In an example, a plurality of combined images comprising the plurality of images is determined, and a plurality of measures of information content is determined, wherein a measure of information content is associated with a combined X-ray image; and wherein the plurality of combined X-ray images is determined such that the measures of information content for the plurality of combined images are substantially the same. In an example, at least one of the combined images only has one image. For example, medical data can be an image set that has ten images with weighting factors of 0.1, six images with a weighting factor of 0.2, two images with a weighting factor of 0.4 and one image with a weighting factor of 1.0. Then in this example, a first combined image can be determined from the ten images with a weighting factor of 0.1, a second combined image can be determined from five images with a weighting factor of 0.2, a third combined image can be determined from an image with a weighting factor of 0.2 and from two images with a weighting factor of 0.4, and a fourth combined image can be determined from the image with a weighting factor of 1.0. In this manner, all of the combined images have a weighting factor of 1.0. In other examples, other numbers of images (e.g. X-ray images) with differing measures of information content can be combined in a similar manner. In other examples, the summed weighting factors for the combined images (e.g. X-ray images) are not the same, but are substantially the same. Referring to an example, similar to the described example above, a number of combined images (e.g. X-ray images) can have summed weighting factors equal to 0.9, 0.8, 1.0, 1.1, 1.05, 0.85, 1.2, such that the summed weighting factors are substantially the same.

In an example, a method for displaying an image of a body part, comprises: providing an image of a body part, wherein the image is associated with a depth within the body part; dividing the image into a plurality of regions; determining a plurality of measures of information content for the plurality of regions, wherein a measure of information content is associated with a region; and displaying the image along with an indicator, wherein the indicator is displayed as a function of the plurality of measures of information content.

Figure 8:
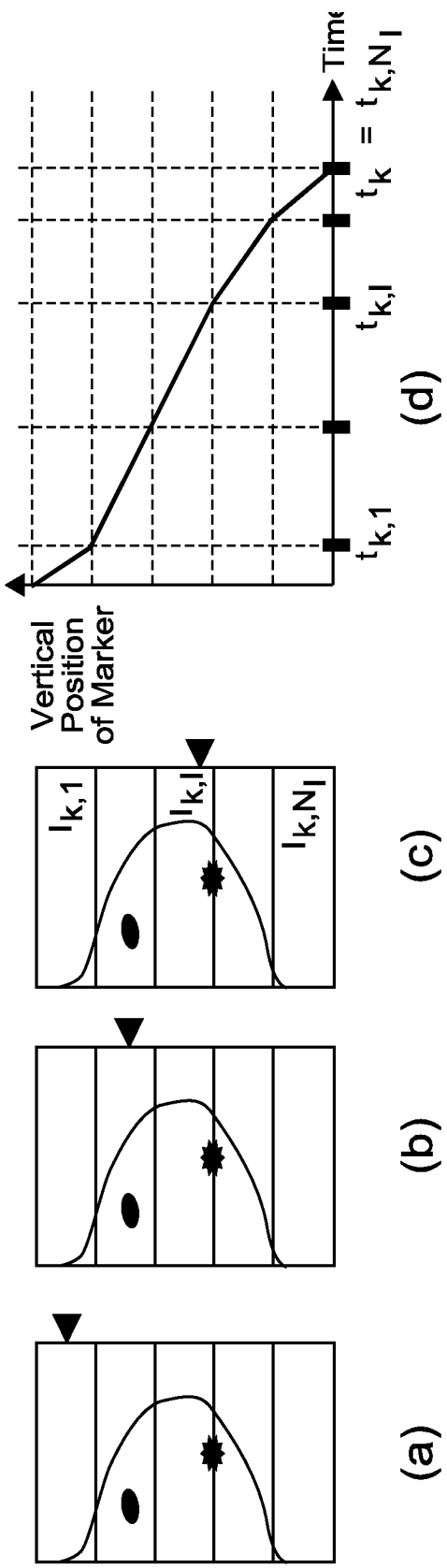
FIG. 8 shows three images (a), (b) and (c) of the same X-ray image of a body part shown at different times, with a marker on the periphery of the images moving downwards in time. Graph (d) illustrates the vertical position of the mark as a function of display time.

In an example, shown for example with reference to FIG. 8, an image is divided into a number of horizontal strips laid one above the other. For example, an image of a breast is divided into sections, one of which is at the top of the breast, one of which is at a centre part of the breast and one of which is at the bottom part of the breast. In an example, the information content for the centre region is determined to be greater than that for the top and bottom regions. In an example, an indicator, such as a marker, can then move vertically down the edge of the image. The speed of the marker can be greater as it moves down the border of the top and bottom regions than the speed it moves down the border of the centre region. In other words, the clinician is given visual information to scan the top and bottom regions quickly, but to spend more time reviewing the centre part that has a higher information content.

Figure 2:
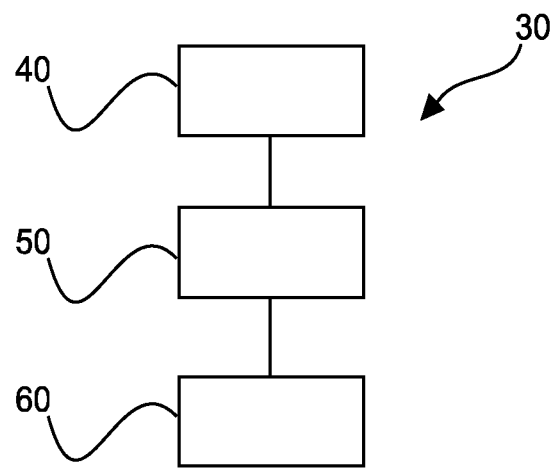
FIG. 2 shows a schematic set up an example of an apparatus for displaying medical image data of a body part.

FIG. 2 shows an example of an apparatus 30 for displaying medical image data of a body part. The apparatus 30 comprises an input unit 40, a processing unit 50 and an output unit 60. The input unit 40 is configured to provide the processing unit 50 with medical data of a body part. The processing unit 50 is also configured to determine subsets of medical image data from the medical data. The processing unit 50 is also configured to determine a plurality of measures of information content for the subsets of medical image data, wherein a measure of information content is associated with a subset of medical image data. The processing unit 50 is further configured to determine a plurality of weighting factors for the subsets of medical image data, wherein a weighting factor is associated with a subset of medical image data and the weighting factor is determined as a function of the measure of information content for that subset of medical image data. The output unit 60 is configured to output data representative of the subsets of medical image data as a function of the plurality of weighting factors.

In an example, medical data of a body part comprises a single 2D image. In this example, the subsets of medical image data can then be regions, zones or areas of that 2D image. For example, medical data of a body part can be a single 2D image, and the subsets of medical image data relate to different horizontal areas of that 2D image. For example, shown for example with reference to FIG. 8, a first subset of the medical image data can mean rows 1-100 of an image, a second subset of the medical image data can mean rows 101-200 of the image, a third subset of the medical image data can mean rows 201-300 of the image etc. In other words, in an example the input unit provides the processor with a single image and the processor can divide that image into subsets of medical image data. For example, the apparatus can be applied to mammography screening to only one 2D image. Weighting factors can then be determined for different sections, zones or areas of that image on the basis of a measure of information content in each section, zone or area. The clinician can then be provided with information relating to, for example, how long they might want to view each section, zone or area.

In an example, the medical data is a volume stack of images, for example 2D CT images through a body or 2D tomography images of a body or 2D MRI images of a body or ultrasound images of a body. In an example, the processor unit determines, or divides, the volume stack into subsets of medical image data. In an example, each subset of medical image data is a single 2D image, for example where each subset is a 2D image relating to a particular depth within the body part and the medical data (such as a volume stack) relates to a series of image at different depths through the body part. Subsets of medical image data can then comprise a series of 2D images of the stack. In an example, a subset of medical image data of a body part comprises an X-ray image. In an example, the subsets of medical image data of a body part comprises X-ray images. In an example, the processor unit determines, or divides, the medical data into subsets of medical image data such that one or more subsets can contain more than one 2D image.

In an example, a subset of medical image data is an image relating to a depth within the body part, for example, this subset of medical image data may be a 2D X-ray image relating to a depth within the body part. In an example, the subsets of medical image data are a plurality of images relating to a plurality of depths within the body part, for example a plurality of 2D X-ray images relating to a plurality of depths within the body part. In an example, the subsets of medical image data are in effect slices that are substantially parallel to each other, oriented normal to the viewer, at different depths through the body part. In other words, when the subsets of medical image data are placed into a stack the subsets of medical image data provides a 3D representation of the body part. In an example, each slice corresponds to a same thickness of the body part, but at different depths through the body part. In an example, neighbouring subsets of medical image data in the subsets of medical image data relate to neighbouring depths within the body part. In other words, by viewing in sequence the subsets of medical image data a viewer can progressively view through the body part at ever decreasing depths. Or to put it another way, the subsets of medical image data can be used to provide 3D information in a step wise fashion of the body part. For example, the X-ray images are in effect slices that are substantially parallel to each other, oriented normal to the viewer, at different depths through the body part. In other words, when the plurality of X-ray images are placed into a stack the plurality of X-ray images provides a 3D representation of the body part. In an example, each slice corresponds to a same thickness of the body part, but at different depths through the body part. In an example, neighbouring X-ray images in a sequence of X-ray images relate to neighbouring depths within the body part. In other words, by viewing in sequence the X-ray images a viewer can progressively view through the body part at ever decreasing depths. Or to put it another way, the sequence of X-ray images can be used to provide 3D information in a step wise fashion of the body part.

In some examples images within a volume stack are not be ordered by their depth within the body part. For example, the preferred depth direction in tomosynthesis is due to the image planes being ordered parallel to the breast support. However, this is not necessarily true for other (fully 3D) modalities, such as MRI, CT, or ultrasound and as such the images could be ordered other than by their depth within the body part. For example, there could be a set of axial, coronal and sagittal image planes through one particular point in the body in case of fully three-dimensional CT or MRI data.

In an example, each of the subset of medical image data is associated with a different depth within the body part. In an example, the medical data comprises a sequence of images at ever increasing depths within the body part. In other words, the subsets of medical image data can comprise a sequence of X-ray images at ever increasing depths within the body part.

In an example, the output unit is configured to display the subsets of medical image data. For, example the output unit can display the subsets of medical image data on a monitor, or screen or other visual display medium. For example, the output unit is configured to display the plurality of X-ray images. For, example the output unit can display the plurality of X-ray images on a monitor, or screen or other visual display medium. In an example, the subsets of medical image data (e.g. plurality of X-ray images) can be shown as a cine-loop of volume data. In an example, a user is able to pause the cine loop on the basis of the measure of information content. For example, when the measure of information content has been indicated to the user as being high the user may wish to pause the cine loop. The user could be provided with visual or audio information relating to the measure of information content in a subset of medical image data (e.g. X-ray image), which could relate to a colour being presented along with an image or relate to the duration an image is being presented or relate to an audio signal that is sounded along with the display of a subset of medical image data (e.g. X-ray image), for example.

In an example, the processing unit determines the measure of information content for a subset of medical image data (e.g. X-ray image) by calculating the Shannon entropy for that subset of medical image data (e.g. X-ray image). The Shannon entropy may be calculated for a part of the subset of medical image data (e.g. X-ray image), or for the entire subset of medical image data (e.g. X-ray image). In an example, the processing unit determines the measure of information content for a subset of medical image data (e.g. X-ray image) by applying an edge response filter or edge response filters to that subset of medical image data (e.g. X-ray image). The response filter or edge response filters may be applied to a part of the subset of medical image data (e.g. X-ray image), or to the entire subset of medical image data (e.g. X-ray image). An edge response filter may be a derivate filter. For example, an edge response filter, derivative filter, or gradient operator, can be used to determine the edge responses within a subset of medical image data (e.g. X-ray image). The number of edge responses found relates to the number of features to be found in that subset of medical image data (e.g. X-ray image), with the number of features relating to the information content within that subset of medical image data (e.g. X-ray image). In an example, the number of features linearly correlates with the number of edges. In an example, the information content linearly correlates with the number of features. In an example, the processing unit determines the measure of information content for a subset of medical image data (e.g. X-ray image) on the basis of brightness (intensity) values in that subset of medical image data (e.g. X-ray image). The brightness (intensity) values may relate to a part of the subset of medical image data (e.g. X-ray image), or to the entire subset of medical image data (e.g. X-ray image). In an example, the processing unit determines the measure of information content for a subset of medical image data (e.g. X-ray image) on the basis of histogram measures relating to the pixels in that subset of medical image data (e.g. X-ray image). Histogram measures may relate to a part of the subset of medical image data (e.g. X-ray image), or to the entire subset of medical image data (e.g. X-ray image). In an example, the processing unit determines the measure of information content for a subset of medical image data (e.g. X-ray image) on the basis of the number of CAD findings within that subset of medical image data (e.g. X-ray image). CAD findings may relate to a part of the subset of medical image data (e.g. X-ray image), or to the entire subset of medical image data (e.g. X-ray image). Computer Aided Detection (CAD) relates to the automatic detection of features or suspected abnormalities, including information such as their location. In an example the processing unit determines the measure of information content for a subset of medical image data (e.g. X-ray image) using any combination of, including some or all of: Shannon entropy; edge response filter or edge response filters; brightness (intensity)

values; histogram measures; and CAD findings. In an example, image processing is used to determine the measure of information content.

The processing unit being configured to determine a plurality of weighting factors for the subsets of medical image data (e.g. plurality of X-ray images), means that the processing unit determines a separate weighting factor for each subset of medical image data (e.g. X-ray image) as a function of the information content for that X-ray image. In an example, the processing unit is configured to determine a weighting factor for a subset of medical image data (e.g. X-ray image) by applying a transfer function to the measure of information content for that subset of medical image data (e.g. X-ray image).

In an example, the processing unit is configured to determine a weighting factor for a subset of medical image data (e.g. X-ray image), by arranging the plurality of measures of information content for the subsets of medical image data (e.g. plurality of X-ray images). In this example, the weighting factor for the subset of medical image data (e.g. X-ray image) is the arranged value for that subset of medical image data (e.g. X-ray image). In an example, the subsets of medical image data (e.g. X-ray images) are arranged linearly with respect to their respective measures of information content. In an example, the subsets of medical image data (e.g. X-ray images) are arranged non-linearly with respect to their respective measures of information content. In an example, the processing unit is configured to determine a weighting factor for a subset of medical image data (e.g. X-ray image), by normalising the plurality of measures of information content for the subsets of medical image data (e.g. plurality of X-ray images). In this example, the weighting factor for the subset of medical image data (e.g. X-ray image) is the normalised value of the measure of information content for that subset of medical image data (e.g. X-ray image). In an example, the normalised values of the measures of information content for the subsets of medical image data (e.g. plurality of X-ray images) has a minimum value of zero and a maximum value of one.

In an example, the output unit is configured to output the subsets of medical image data (e.g. plurality of X-ray images), wherein a subset of medical image data (e.g. X-ray image) is output as a function of the weighting factor for that subset of medical image data (e.g. X-ray image).

In an example, the processing unit is configured to determine a plurality of time factors for the subsets of medical image data (e.g. plurality of X-ray images), wherein a time factor is associated with a subset of medical image data (e.g. X-ray image) and the time factor is determined as a function of the weighting factor for that subset of medical image data (e.g. X-ray image). In an example, the time factor is a linear function of the weighting factor. In an example, the weighting factor is a non-linear function of the time factor. In an example, the time factor for a subset of medical image data (e.g. X-ray image) is proportional to the weighting factor for that subset of medical image data (e.g. X-ray image). In an example, the time factor is equal to the weighting factor.

In other words each subset of medical image data (e.g. X-ray image or part of an X-ray image) has an associated time factor determined for it on the basis of the weighting factor for each subset of medical image data (e.g. X-ray image or part of an X-ray image). In this manner, the apparatus can output or display the subsets of medical image data (e.g. plurality of X-ray images or parts of an X-ray image) where individual subsets of medical image data (e.g. X-ray images or parts of an X-ray image) can be displayed taking into account a time factor, derived from the information content in the X-ray images. Therefore, the clinician is provided with information relating to the time they may wish to take in reviewing a particular subset of medical image data (e.g. X-ray image, or a particular part of an X-ray image, or X-ray images, or a plurality of X-ray images), enabling them to focus more time on the pertinent subsets of medical image data (e.g. X-ray images).

According to an example, the processing unit is configured to determine a plurality of durations of time for the subsets of medical image data, wherein a duration of time is associated with a subset of medical image data and the duration of time is determined as a function of the weighting factor for that subset of medical image data. The output unit is configured to display the subsets of medical image data as a function of the plurality of durations of time.

In an example, the duration of time is determined as a function of the time factor for that subset of medical image data (e.g. X-ray image). In an example, a subset of medical image data (e.g. X-ray image) of the subsets of medical image data (e.g. plurality of X-ray images) is displayed for a time equal to the determined duration of time for that subset of medical image data (e.g. X-ray image). In an example, each of the subsets of medical image data (e.g. X-ray image) in the subsets of medical image data (e.g. plurality of X-ray images) is shown for a time equal to the determined duration of time for each of the subsets of medical image data (e.g. X-ray image). In an example, the duration of time is a linear function of the weighting factor or time factor. In an example, the duration of time is a non-linear function of the weighting factor or time factor. In an example, the duration of time for a subset of medical image data (e.g. X-ray image) is proportional to the weighting factor or time factor for that subset of medical image data (e.g. X-ray image). In an example, the processing unit is configured to determine a duration of time for a subset of medical image data (e.g. X-ray image) by multiplying a total display time for the subsets of medical image data (e.g. plurality of X-ray images) by the weighting factor for the subset of medical image data (e.g. X-ray image), divided by the summation of weighting factors for the subsets of medical image data (e.g. plurality of X-ray images). The time factors could similarly be used to determine a duration of time.

In an example, the processing unit is configured to determine a number of frame repetitions for a subset of medical image data (e.g. X-ray image) that is proportional to the duration of time for that subset of medical image data (e.g. X-ray image), and wherein the output unit is configured to display the subset of medical image data (e.g. X-ray image) for the number of frame repetitions for that subset of medical image data (e.g. X-ray image). In an example, the processing unit is configured to determine a number of frame repetitions for a subset of medical image data (e.g. X-ray image) by multiplying a total number of display frames for the subsets of medical image data (e.g. X-ray image) by the weighting factor for that subset of medical image data (e.g. X-ray image), divided by the summation of weighting factors for the subsets of medical image data (e.g. plurality of X-ray images). Similarly, the processing unit is configured to determine a number of frame repetitions for a subset of medical image data (e.g. X-ray image) on the basis of the time factors (or the durations of time). In this manner, the numbers of frames for which each subset of medical image data (e.g. X-ray image) of the subsets of medical image data (e.g. plurality of X-ray images) is displayed can be determined. For example, the number of frames for which a subset of medical image data (e.g. X-ray image) of the subsets of medical image data (e.g. plurality of X-ray images) is displayed can be determined. In an example, the total number of display frames is input by a user. In other words, in an example, as the display frame rate for display systems can be constant on a viewing device, a variable frame rate can be mimicked by repeating each frame in the series according to a transfer function, which is applied to an entropy measure.

In an example, shown for example with reference to FIG. 8, an image or slice reconstruction is sub-divided into vertical or horizontal regions, dependent upon a clinician or radiologists preference in reading or reviewing the slice reconstruction in a left to right, or right to left, or top to bottom, or bottom to top direction. In an example, normalized local entropy is computed in each sub-image in order to sub-divide the total reading time of the current slice into time sub-intervals corresponding to the sub-images, as described above. In an example, an indicator can be displayed marking both the current sub-image and the suggested reading time for that current sub-image. In an example, where for example an image is sub-divided into horizontal sub-images and where the clinician wishes to view images in a top to bottom manner, a marker is moved along the vertical border of the image according to the computed durations of time, as a visual indicator for steering (local) reading time of the radiologist per region in the current slice reconstruction. In an example, this procedure can be carried out for a single image (such as a 2D X-ray mammogram) or for a series of images of a volume stack, such as 2D X-ray tomography or X-Ray CT images or MRI images.

According to an example, the processing unit is configured to determine a plurality of indicators for the subsets of medical image data, wherein an indicator is associated with a subset of medical image data and the indicator is a function of the weighting factor for that subset of medical image data. The output unit is configured to output the plurality of indicators.

In an example, the output unit is configured to display the subsets of medical image data (e.g. plurality X-ray images), and to display an indicator of the plurality of indicators that is associated with a subset of medical image data (e.g. X-ray image) of the subsets of medical image data (e.g. plurality of X-ray images) along with the display of the subset of medical image data (e.g. X-ray image). In an example, the output unit is configured to display the subsets of medical image data (e.g. plurality of X-ray images), and to sound an indicator of the plurality of indicators that is associated with a subset of medical image data (e.g. X-ray image) of the subsets of medical image data (e.g. plurality of X-ray images) along with the display of the subset of medical image data (e.g. X-ray image).

According to an example, the medical data comprises a plurality of images, and the processing unit is configured to determine at least one subset of medical image data that is a combined image of at least two of the plurality of images. The processing unit is also configured to determine the at least one subset of medical image data, that is a combined image, such that the weighting factor for the at least one subset of medical image data that is a combined image is substantially the same as the weighting factor for a different subset of medical image data or substantially the same as a specified target value.

In an example, the total number of subsets of medical image data is N wherein one or more of those subsets of medical image data is a combined image or slab. Therefore, in an example medical data, for example a volume stack of images, can be separated into N subsets or slabs, which could have varying thicknesses, but these are separated such that each slab has approximately similar information content (i.e., weighting factors). In an example, a user specifies N, the number of slabs required, and the processing unit determines the N subsets of medical image data, a number of which are combined images, an information content of 1/N per subset of the information content in the volume stack is arrived at. In other words, the weight factor is a function of, or specified by, the input value N. In this manner, the case where the processing unit determines a combined image such that its weighting factor is substantially the same as that for another subset is special case of a specified target value.

According to an example, the processing unit is configured to determine an information content for the subset of medical image data that is the combined image by determining information contents for the at least two of the plurality of images forming the combined image. The processing unit then determines a weighting factor for the subset of medical image data that is the combined image by determining weighting factors for the at least two of the plurality of images forming the combined image and summing those weighting factors;

According to an example, the processing unit is configured to determine an information content for the subset of medical image data that is the combined image by determining a single information content for the combined image. The processing unit is then configured to determine a weighting factor for the subset of medical image data that is the combined image by determining a single weighting factor for the combined image.

In an example, the plurality of images comprises X-ray images. In an example, the plurality of images comprises MRI images. In an example, the plurality of images comprises Ultrasound images. In an example, the plurality of images comprises images acquired by a tomography arrangement. In an example, the plurality of images comprises images acquired by a CT arrangement. In an example, the plurality of images comprises images acquired by an MRI arrangement. In an example, the plurality of images comprises images acquired by an ultrasound arrangement.

In an example, the processing unit is configured to determine a combined X-ray image from a subset of X-ray images of a plurality of X-ray images. The processing unit is configured to determine a measure of information content for the combined X-ray image. The processing unit is configured to determine the combined X-ray image such that the measure of information content for the combined X-ray image is substantially the same as the measure of information content for at least one of the plurality of X-ray images other than those in the subset of X-ray images.

In an example, the processing unit is configured to determine a combined X-ray image from a subset of X-ray images of a plurality of X-ray images. The processing unit is configured to determine a measure of information content for the combined X-ray image. The processing unit is configured to determine at least one second combined X-ray image from at least one second subset of X-ray images of the plurality of X-ray images containing X-ray images different to those in the first subset of X-ray images. The processing unit is configured to determine at least one measure of information content for the at least one second combined X-ray image. The processing unit is configured to determine the first combined X-ray image and to determine the at least one second combined X-ray image such that the measure of information content for the first combined X-ray image is substantially the same as the at least one measure of information content for the at least one second combined X-ray image.

In an example, there is provided an apparatus for displaying X-ray images of a body part, comprising: an input unit; a processing unit; and an output unit; wherein, the input unit is configured to provide the processing unit with a plurality of X-ray images of a body part relating to a plurality of depths within the body part, wherein an X-ray image is associated with a depth within the body part; wherein the processing unit is configured to determine a first combined X-ray image from a first subset of X-ray images of the plurality of X-ray images, and to determine at least one second combined X-ray image from at least a second subset of X-ray images of the plurality of X-ray images containing X-ray images different to those in the first subset of X-ray images; wherein the processing unit is configured to determine a measure of information content for the first combined X-ray image, and to determine at least one measure of information content for the at least one second combined X-ray image; wherein the processing unit is configured to determine the first combined X-ray image and to determine the at least one second combined X-ray image such that the measure of information content for the first combined X-ray image is substantially the same as the at least one measure of information content for the at least one second combined X-ray image; and wherein the output unit is configured to output data representative of the first combined X-ray image and the at least one second combined X-ray image.

In an example, the output unit is configured to display the first combined X-ray image and the at least one second combined X-ray image.

In an example, neighbouring slices in a stack are combined. For example, slices are only combined if they relate to adjacent depth of the body part. In an example, the means by which the slices or images are combined is non-linear, hence the measure of information content is also non-linear, in that the summation of the measures of information content for the individual images (e.g. X-ray images) of a combined image is not the same as the measure of information content for the combined image e.g. (combined X-ray image).

In an example, the means by which the measure of information content is determined is linear, in that the summation of the measures of information content for the individual images (e.g. X-ray images) of a combined image is substantially the same as the measure of information content for the combined image e.g. (combined X-ray image).

In an example, the weighting factor for a subset of medical image data that is a combined image is determined iteratively. For example, an image (e.g. X-ray image) is combined with an adjacent image (e.g. X-ray image) and the measure of information content is calculated for this combined image following which the weighting factor is calculated. If necessary, a further image (e.g. X-ray image) adjacent to one of the images (e.g. X-ray images) making up the combined image (e.g. combined X-ray image) is combined with the images (e.g. X-ray images) already making up the combined image and/or an image (e.g. X-ray image) making up the combined image is removed from the combined image, and the measure of information content and weighting factor again calculated. This process can be conducted until the weighting factor for the subset of medical image data that comprises the combined image substantially matches that for another subset of medical image data or any other specified target value. In an example, more than one or indeed all of the subsets of medical image data can be formed of combined images, and the above iterative process can be applied across a number of or all of the subsets until the weighting factors for those number of subsets or of all of the subsets is substantially the same. Any suitable minimisation routine, could be used in such an iterative process. Other mechanisms for determining the weighting factors for such combined images can be used. If required, a subset of medical image data that is a combined image can comprise a single image (e.g. X-ray image).

In an example, there is provided an apparatus for displaying images of a body part, comprising: an input unit; a processing unit; and an output unit; wherein, the input unit is configured to provide the processing unit with a plurality of images of a body part relating to a plurality of depths within the body part, wherein an image is associated with a depth within the body part; wherein, the processing unit is configured to determine a plurality of measures of information content for the plurality of images, wherein a measure of information content is associated with an image; wherein, the processing unit is configured to determine a plurality of weighting factors for the plurality of images, wherein a weighting factor is associated with an X-ray image and the weighting factor is determined as a function of the measure of information content for that X-ray image; and wherein, the output unit is configured to output data representative of the plurality of X-ray images as a function of the plurality of weighting factors.

In an example, there is provided an apparatus for displaying images of a body part, comprising: an input unit; a processing unit; and an output unit; wherein, the input unit is configured to provide the processing unit with a plurality of images of a body part relating to a plurality of depths within the body part, wherein an image is associated with a depth within the body part; wherein the processing unit is configured to determine a first combined image from a first subset of images of the plurality of images, and to determine at least one second combined image from at least a second subset of images of the plurality of images containing images different to those in the first subset of images; wherein the processing unit is configured to determine a measure of information content for the first combined image, and to determine at least one measure of information content for the at least one second combined image; wherein the processing unit is configured to determine the first combined image and to determine the at least one second combined image such that the measure of information content for the first combined image is substantially the same as the at least one measure of information content for the at least one second combined image; and wherein the output unit is configured to output data representative of the first combined image and the at least one second combined image.

In an example, there is provided an apparatus for displaying an image of a body part, comprising: an input unit; a processing unit; and an output unit; wherein the input unit is configured to provide the processing unit with an image of a body part, wherein the image is associated with a depth within the body part; wherein the processing unit is configured to divide the image into a plurality of regions; wherein, the processing unit is configured to determine a plurality of measures of information content for the plurality of regions, wherein a measure of information content is associated with a region; and wherein, the output unit is configured to display the image along with an indicator, wherein the indicator is displayed as a function of the plurality of measures of information content.

Figure 3:
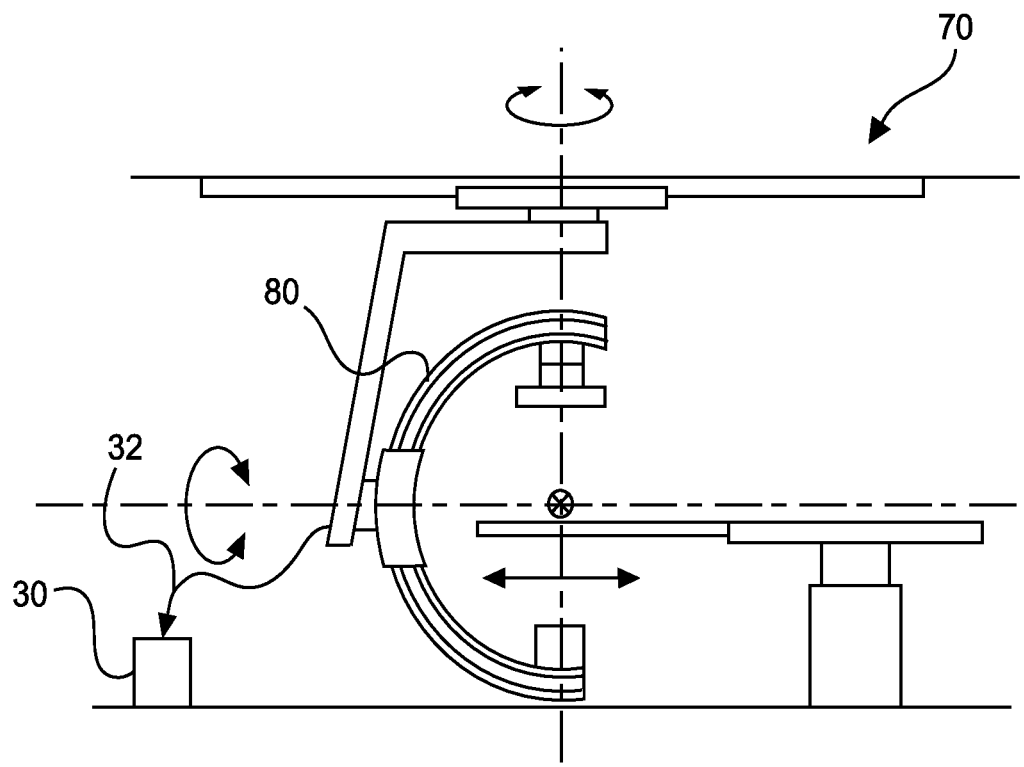
FIG. 3 shows a schematic set up an example of a medical system for displaying medical image data of a body part.

FIG. 3. shows a medical system 70 for displaying medical image data of a body part. The system 70 comprises an image acquisition unit 80, an apparatus 30 for displaying medical image data of a body part, and a display unit 90 (not shown, but a device such as a visual display unit VDU, or other type of monitor or display means). The apparatus 30 is provided as any of the examples referred above with respect to FIG. 2. The image acquisition unit 80 is configured to provide the medical image data of a body part to the apparatus 30 via communication means 32, such as a communication cable. The display unit 90 is configured to display the subsets of medical image data.

In an example, the image acquisition unit comprises an X-ray imaging device, for example, a tomosynthesis arrangement, or a CT arrangement. In an example, the image acquisition unit comprises an ultrasound arrangement or a MRI arrangement.

Figure 4:
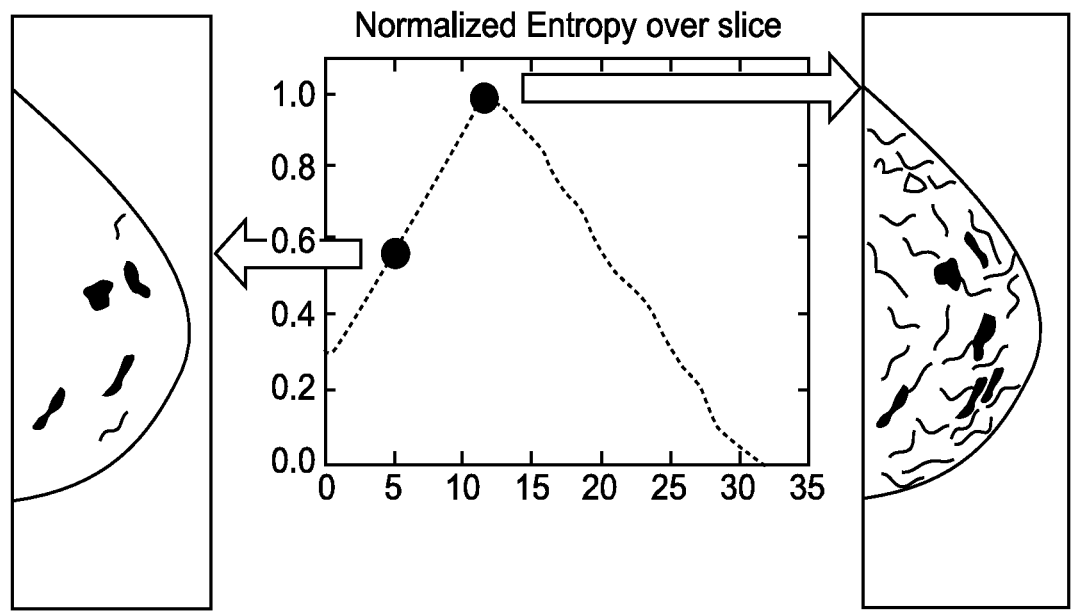
FIG. 4 shows schematic representations of X-ray images, or slices, of an image set. Between the two images is a graph illustrating a measure of information content over the series of slices of the image set.
Figure 5:
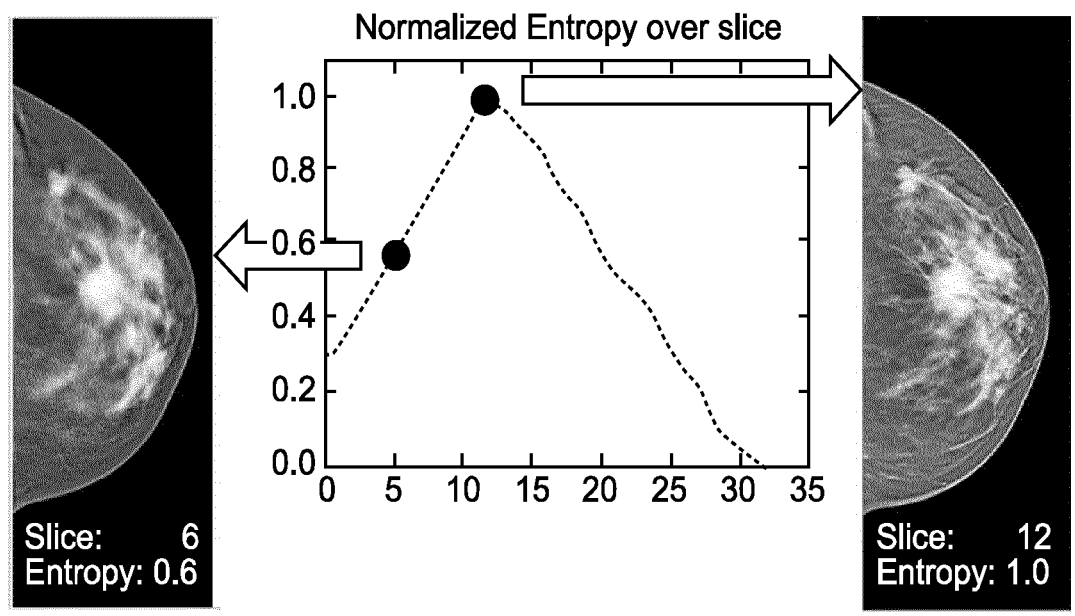
FIG. 5 shows the same information is presented in FIG. 4, where the schematic representations are replaced by X-ray images.
Figure 6:
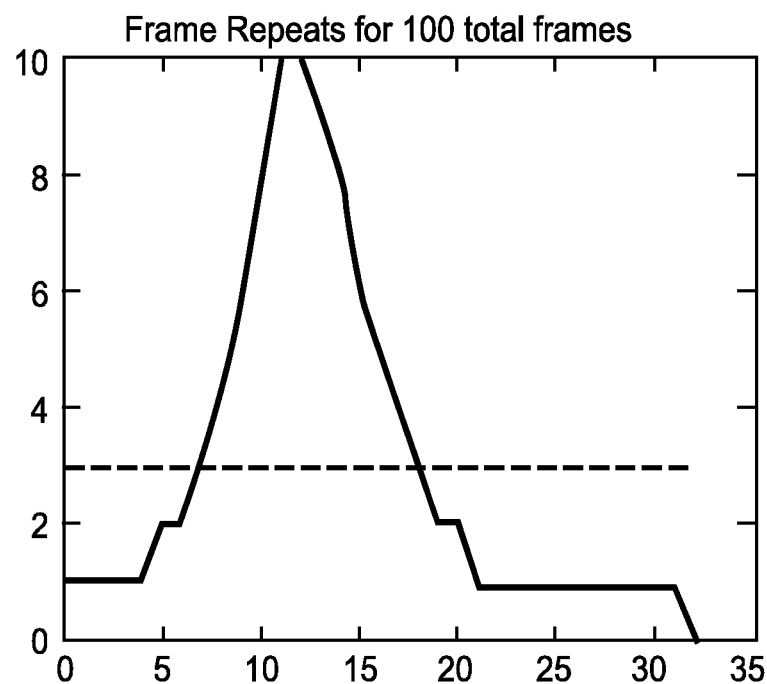
FIG. 6 shows the number of times an X-ray image is displayed as a function of the image number of an image set.

FIGS. 4 and 5 show schematic X-ray images, or slices, of an X-ray image set. Between the two images is a graph illustrating a measure of information content over the series of slices of the X-ray image set. Tomosynthesis imaging is characterized by out-of-plane blurring of structures due to the limited tomographic angle acquisition. For example, a reconstruction of a subcutaneous fat layer will be affected by out-of-plane artifacts that originate from dense tissue structures deeper in the breast. Hence, it will appear more blurred and more homogenous than a reconstruction of a second slice, which contains clinical structures such as calcifications, lesions or fibro-glandular structures. Although the reconstruction of the subcutaneous fat layer contains less information than the second slice, both slice reconstructions are in existing systems displayed equally long in a cine-loop of all reconstructed slices. In FIGS. 4 and 5, exemplary slice, or X-ray image, reconstructions are shown of a slice of low information content (left) and high information content (right) in a stack of 32 tomosynthesis slice reconstructions according to the presently described apparatus, method and system. The centre graph in FIGS. 4 and 5 illustrates a measure of information content for the 32 X-ray images. In this example, the measure of information content is shown as a normalised information content computed with an entropy measure over the series of slice reconstructions. In this way, it is possible to display frames of medical image data according to the amount of image information contain. The frame rate, or effective frame rate achieved by showing a particular frame a determined number of times, of a cine loop of tomosynthesis volume data is adapted to the information content in the displayed slice reconstruction. In this example, this is achieved by computing an entropy measure in each slice reconstruction, which is mapped to a number of frame repetitions, or display time, of this slice in the cine loop with a transfer function. The case where the entropy measure, or in other words measure of information content, is mapped to a number of frame repetitions of particular slices is shown in FIG. 6. In FIG. 6 the number of times a particular X-ray image is repeatedly shown is illustrated as a function of the X-ray image number in the volume stack. There are 32 individual x-ray images, two of which are shown ten times and two of which are shown six times etc. The total number of frame repetitions is 100, and the two X-ray images shown 10 times have the greatest measure of information content in those X-ray images. Some X-ray images have relatively low measures of information content, and are shown only once. In this manner, those images with the greatest measure of information content are automatically shown to the clinician for the longest time. Alternatively, reconstructed slices can be combined in slabs of variable slice thickness, which is computed such that each slab contains the same amount of image information. Each combined slab can then be shown the same amount of time, because it contains the same amount of information. Furthermore, using the measure of information content a visual marker (number, colour code) can be displayed together with current frame, indicating the information content of the current frame with respect to the other frames in the series.

The information content within an X-ray image is computed with the Shannon entropy. The Shannon entropy is computed for X-ray images within the series of data to be displayed, and then normalised to the range (0, 1). Such a normalised measure of information content constitutes a weighting factor that can be used to display the X-ray images as required. The centre graph of FIGS. 4 and 5 shows such a normalised measure of information content or weighting factor. Other measures for estimating information content within one frame, can be derived from, for example, edge response filters (derivate filters), brightness (intensity) values, histogram measures, the number of CAD findings within a frame and combinations thereof.

As discussed above, the information content with frame is computed with the Shannon entropy. The Shannon entropy H is computed for a discrete random variable X with possible values $X \in \{x_1, \ldots, x_N\}$ and corresponding probability density function p(X) via $$H(X) = -\Sigma_{i=1}^{N} p(x_i) \log_2 p(x_i) \quad (1)$$

Figure 7:
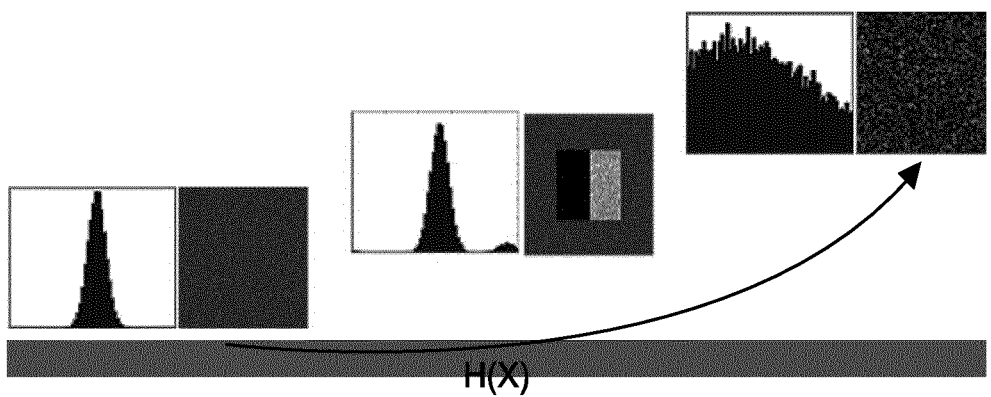
FIG. 7 shows three images with increasing Shannon entropy. Each image is depicted together with its respective histogram.

FIG. 7 shows three images with increasing Shannon entropy value H(X). Note, that the maximum entropy $H_{max} = \log_2 N$ is obtained for a uniform probability density function.

The Shannon entropy can be computed for each slice reconstruction image $I_k = I(x, y, z_k)$ in a tomosynthesis volume stack $S = \{I_k: k=1, \ldots, N_K\}$ as a histogram-based measure. Without loss of generality, it can be assumed that the image is normalized to the data range [0, 1], i.e. it holds $0 \leq I(x_i, y_j, z_k) \leq 1$ for all voxels $(x_i, y_j, z_k)$, $i=1, \ldots, N_I$, $j=1, \ldots, N_J$, $k=1, \ldots, N_K$ in the reconstructed volume stack S. The data range [0, 1] is then separated into $N_H$ equally spaced bins $$b_h = \left[ \frac{h-1}{N_H}, \frac{h}{N_H} \right],$$

$h=1, \ldots, N_H$ and a density function $p_k$ is computed from the histogram of the slice reconstruction $I_k$ with bins $b_h$. Using equation (1), the normalized entropy in each slice reconstruction image $I_k$ is derived as $$H_k := H(I_k)/H_{max} = -\frac{1}{\log_2 N_H} \sum_{h=1}^{N_H} p_k(b_h) \log_2 p_k(b_h) \quad (2)$$

by normalization with the maximum entropy $H_{max} = \log_2 N_H$.

The normalized entropy measure $H_k$, which satisfies $0 \leq H_k \leq 1$, is now computed for all slice reconstructions $I_k$ within the volume stack S in order to control the display time of the respective image or the duration time of a corresponding visual or acoustic signal, or be used to combine slices into slabs having the same measure of information content. To this end, the display time $t_k = f(H_k)$ is computed as a function of the normalized entropy $H_k$. The transfer function f, which maps the entropy of each slice to the display time, can be implemented as a linear function or a more general monotonically increasing transfer function such that with increasing entropy the display time will increase, too.

In one example, a total reading time T is suggested from the algorithm for a particular set of medical data and a particular radiologist operating the system. The suggested reading time T may be computed from both the expected average reading time of the radiologist (measured from previous readings of comparable medical data sets) and from the image or acquisition data (total entropy of the whole stack H(S), total number of slices in stack, etc.). In a first step, the total reading time T is divided into reading times $t_k$ for the $N_K$ slice images $I_k$ using a transfer function $f(H_k)$ as described above. In a second step, the method is repeated for each slice reconstruction to derive suggested reading times $t_{k,l}$, $l=1, \ldots, N_l$ for regions (sub-images) $I_{k,l}$, of each slice reconstruction $I_k$.

According to an example, a slice reconstruction is subdivided into vertical or horizontal regions $I_{k,l}$, dependent on the radiologists preference to read a slice reconstruction in left-right (right-left) or top-bottom (bottom-top) direction, see FIG. 8. Then, the normalized local entropy is computed in each sub-image $I_{k,l}$ in order to subdivide the total reading time $t_k$ of the current slice into $N_l$ sub-intervals $t_{k,l}$ corresponding to the sub-images $I_{k,l}$ with the methods described above. Finally, an indicator is displayed marking both the current sub-image $I_{k,l}$ and the suggested reading time $t_{k,l}$. With horizontal (vertical) sub-images, a marker is moved along the vertical (horizontal) border of the image according to the precomputed sub-intervals $t_{k,l}$ as a visual indicator for steering the (local) reading time of the radiologist per region in the current slice reconstruction, see FIG. 8.

Referring to FIG. 8 in more detail, an illustration of the display of a triangular marker (a-c) according to the computed display times $t_{k,l}$ per sub-image $I_{k,l}$ is shown. Image (d) shows the vertical position of the maker as a function of display time. Note that the display times $t_{k,l}$ are shown in Figure (d) as cumulative display times. The marker will be moved faster in the first and last sub-image due to the low information content. In sub-regions with higher information content, illustrated by the two lesions in the top two frames or regions of the image shown at times (a), (b) and (c), the marker will be moved slower along the vertical border of the image, see the marker-position over time curve (d).

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for processing medical image data of a body part, comprising:
    a processor configured to:
        receive the medical data of the body part;
        determine a plurality of subsets of medical image data;
        calculate a plurality of measures of information content for the subsets of medical image data, wherein each measure of information content is associated with a corresponding subset of medical image data;
        use the measures of information content to determine a plurality of weighting factors for the subsets of medical image data, wherein each weighting factor is associated with the corresponding subset of medical image data;

use the weighting factors to determine a plurality of durations of time for the subsets of medical image data, wherein each duration of time is associated with a corresponding subset of medical image data; and a display configured to output the subsets of medical image data in direct proportion to the corresponding duration of time.

2. The apparatus according to claim 1, wherein the processor is configured to determine a plurality of indicators for the subsets of medical image data, wherein each indicator is associated with the corresponding subset of medical image data, wherein the indicator is based on the weighting factor for the subset of medical image data; and wherein the display is configured to output the plurality of indicators.

3. The apparatus according to claim 1, wherein the medical data comprises a plurality of images, wherein the processor is configured to determine at least one subset of medical image data that is a combined image of at least two of the plurality of images, wherein the processor is configured to determine the at least one subset of medical image data that is a combined image such that the weighting factor for the at least one subset of medical image data that is a combined image is substantially the same as the weighting factor for a different subset of medical image data or substantially the same as a specified target value.

4. The apparatus according to claim 3, wherein the processor is configured to:

determine an information content for the subset of medical image data that is the combined image by determining information contents for the at least two of the plurality of images forming the combined image, and determine a weighting factor for the subset of medical image data that is the combined image by determining weighting factors for the at least two of the plurality of images forming the combined image and summing those weighting factors; or determine an information content for the subset of medical image data that is the combined image by determining a single information content for the combined image, and determine a weighting factor for the subset of medical image data that is the combined image by determining a single weighting factor for the combined image.

5. A medical system for processing medical image data of a body part, the system comprising:

an image acquisition device configured to acquire the medical image data of a body part; and an apparatus for processing the medical image data of the body part, the apparatus comprising:

a processor configured to:

receive the medical image data from the image acquisition device;

determine a plurality of subsets of the received medical image data;

calculate a plurality of measures of information content for the subsets of medical image data, wherein each measure of information content is associated with a corresponding subset of medical image data;

use the measures of information content to determine a plurality of weighting factors for the subsets of medical image data, wherein each weighting factor is associated with the corresponding subset of medical image data;

use the weighting factors to determine a plurality of durations of time for the subsets of medical image data, wherein each duration of time is associated with a corresponding subset of medical image data; and a display configured to output the subsets of medical image data in direct proportion to the corresponding duration of time.

6. A method for processing medical image data of a body part, comprising:

acquiring the medical image data of the body part;

determining a plurality of subsets of the acquired medical image data;

calculating a plurality of measures of information content for the subsets of medical image data, wherein each measure of information content is associated with a corresponding subset of medical image data;

using the measures of information content to determine a plurality of weighting factors for the subsets of medical image data, wherein each weighting factor is associated with a corresponding subset of medical image data;

using the weighting factors to determine a plurality of durations of time for the subsets of medical image data, wherein each duration of time is associated with a corresponding subset of medical image data; and displaying the subsets of medical image data in direct proportion to the corresponding duration of time.

7. The method according to claim 6, further comprising:

determining a plurality of indicators for the subsets of medical image data, wherein an indicator is associated with a subset of medical image data, and the indicator is based on the weighting factor for the subset of medical image data; and outputting the plurality of indicators.

8. The method according to claim 7, further comprising displaying or sounding the indicator of the plurality of indicators that is associated with a corresponding subset of medical image data.

9. The method according to claim 6, wherein the medical data comprises a plurality of images, and the method further comprises determining at least one subset of medical image data that is a combined image of at least two of the plurality of images, and determining the at least one subset of medical image data that is a combined image such that the weighting factor for the at least one subset of medical image data that is a combined image is substantially the same as the weighting factor for a different subset of medical image data or substantially the same as a specified target value.

10. The method according to claim 9, further comprising determining an information content for the subset of medical image data that is the combined image by determining information contents for the at least two of the plurality of images forming the combined image, and determining a weighting factor for the subset of medical image data that is the combined image by determining weighting factors for the at least two of the plurality of images forming the combined image and summing those weighting factors.

11. The method according to claim 9, further comprising determining an information content for the subset of medical image data that is the combined image by determining a single information content for the combined image, and determining a weighting factor for the subset of medical image data that is the combined image by determining a single weighting factor for the combined image.

12. A non-transitory computer-readable medium having one or more executable instructions stored thereon, which when executed by a processor, cause the processor to perform a method for processing medical image data of a body part, the method comprising:
- acquiring the medical image data of the body part;
- determining a plurality of subsets of the acquired medical image data;
- calculating a plurality of measures of information content for the subsets of medical image data, wherein each measure of information content is associated with a corresponding subset of medical image data;
- using the measures of content to determine a plurality of weighting factors for the subsets of medical image data, wherein each weighting factor is associated with a corresponding subset of medical image data;
- using the weighting factors to determine a plurality of durations of time for the subsets of medical image data, wherein each duration of time is associated with a corresponding subset of medical image data; and
- displaying the subsets of medical image data in direct proportion to the corresponding duration of time.

* * * * *